United States Patent [19]
Choy et al.

[11] Patent Number: 5,679,687
[45] Date of Patent: Oct. 21, 1997

[54] IRREVERSIBLE HIV PROTEASE INHIBITORS, COMPOSITIONS CONTAINING SAME AND PROCESS FOR THE PREPARATION THEREOF

[75] Inventors: Nakyen Choy; Hoil Choi; Chi-Hyo Park; Young-Chan Son; Chang-Sun Lee; Heungsik Yoon; Sung-Chun Kim; Jong-Sung Koh; Chung-Ryeol Kim, all of Daejeon, Rep. of Korea

[73] Assignee: LG Chemical Limited, Seoul, Rep. of Korea

[21] Appl. No.: 659,794

[22] Filed: Jun. 6, 1996

Related U.S. Application Data

[63] Continuation-in-part of Ser. No. 341,352, Nov. 17, 1994, which is a continuation-in-part of Ser. No. 159,382, Nov. 30, 1993, Pat. No. 5,587,388.

[30] Foreign Application Priority Data

Dec. 8, 1994 [KR] Rep. of Korea ............... 92-33270

[51] Int. Cl.$^6$ .......... A61K 31/47; A61K 31/335; C07D 217/16; C07D 217/14
[52] U.S. Cl. .......... 514/307; 514/314; 514/475; 546/146; 546/169; 549/552
[58] Field of Search .......... 546/146, 169; 549/552; 514/307, 314, 475

[56] References Cited

U.S. PATENT DOCUMENTS 5,545,750  8/1996  Kempf et al. .......... 564/360
5,587,388  12/1996  Kim et al. .......... 514/314

Primary Examiner—José G. Dees
Assistant Examiner—Mary C. Cebulak
Attorney, Agent, or Firm—Anderson Kill & Olick, P.C.

[57] ABSTRACT

The present invention relates to novel compounds of formula (I) which have inhibitory activity against human immunodeficiency virus ("HIV") protease, a process for the preparation thereof, and compositions for prevention or treatment of AIDS by HIV infection comprising the above compounds as active ingredients.

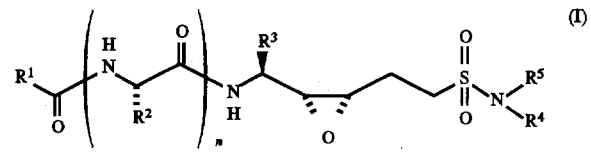

wherein:

$R^1$ is an aromatic group, a nitrogen-containing aromatic group, $C_{1-4}$ alkyl group optionally substituted with an aromatic group or a nitrogen-containing aromatic group, $C_{1-4}$ alkoxy group optionally substituted with an aromatic group or a nitrogen-containing aromatic group;

$R^2$ is an amino acid residue or a $C_{1-8}$ alkyl group substituted with a $C_{1-4}$ alkylsulfonyl group;

$R^3$ is a $C_{1-4}$ alkyl group optionally substituted with an aromatic group;

$R^4$ is hydrogen or a $C_{1-4}$ alkyl group;

$R^5$ is an aromatic group, a $C_{1-10}$ alkyl group or a $C_{1-4}$ alkyl groups optionally substituted with an aromatic group; and n is 1 or 2.

9 Claims, No Drawings

IRREVERSIBLE HIV PROTEASE INHIBITORS, COMPOSITIONS CONTAINING SAME AND PROCESS FOR THE PREPARATION THEREOF

CROSS REFERENCE TO RELATED APPLICATION

This application is a continuation-in-part application of U.S. Ser. No. 08/341,352 filed on Nov. 17, 1994, which is, in turn, a continuation-in-part application of U.S. Ser. No. 08/159,382 filed on Nov. 30, 1993, now U.S. Pat. No. 5,587,388.

FIELD OF THE INVENTION

The present invention relates to novel compounds for inhibiting human immunodeficiency virus ("HIV") protease and pharmaceutical compositions for the prevention or treatment of AIDS(acquired immuno-deficiency syndrome) caused by HIV infection containing the compounds as active ingredients.

BACKGROUND OF THE INVENTION

HIV-1 which is known to cause AIDS(acquired immunodeficiency syndrome) is one of retroviruses which contain their genetic information in RNA; and consists of a core, envelope proteins and a lipid membrane. The HIV core comprising two single-stranded RNA and reverse transcriptase is enclosed by envelope proteins, which are, in turn, enclosed by a lipid membrane.

The reverse transcriptase makes double-stranded DNA from a single-stranded RNA template and, consequently, only retroviruses, i.e., RNA viruses, have a reverse transcriptase. When retroviruses infect a host, the reverse transcriptase makes double-stranded DNA from a single-stranded virus RNA template. The resulting virus DNA is grafted into the host chromosome by integrase, and the transformed host makes new virus RNAs as well as virus proteins by using the host enzyme mechanism. The proteins thus produced are modified by host or virus enzymes to form new viruses. One important enzyme among the protein-modifying enzymes mentioned above is protease, which proteolyzes polyproteins into structural proteins and enzymes required for the virus replication.

Among the proteases of retroviruses, HIV protease has been studied most extensively. As mentioned above, HIV does not synthesize envelope proteins and enzymes using mRNA. Instead, polyproteins, such as Gag protein(P55) and Gag-pol(P165) protein, are processed by HIV protease into structural envelope proteins and functional enzymes e.g., reverse transcriptase and integrase, which are essential for virus replication. Inhibition of the protease activity would thus prevent virus replication, and indeed, previous studies have shown that viruses without functional proteases are incapable of inducing infection (Kohl et al., *Proc. Nat. Acad. Sci.*, U.S.A., 85, 4686–4690(1988); and Peng et al., *J. Virol.*, 63, 2550(1989)). Accordingly, HIV protease inhibitors have been considered as a potential AIDS treating agent.

HIV protease consists of 99 amino acids and its structure was determined by X-ray crystallography(Navia et al., *Nature* 337, 615–620(1989); Wlodawer et al., *Science*, 245, 616–621(1989); and Miller et al., *Science*, 246, 1149–1152 (1989)).

HIV protease is present in a dimeric form; each monomer has a molecular weight of 10,793 daltons. HIV protease is classified as an aspartic protease since it is known to have the typical sequence of Asp-Thr-Gly at the active site.

In this connection, recent studies on HIV protease inhibitors have been focused on the development of compounds having a structure similar to the transition state of the enzyme with the expectation that they would have a high affinity to the protease (see Roberts et al., *Science*, 248, 358(1990); EP Publication Nos. 0337714, 0346847, 0356223, 0352000, 0357332, 0362002, 0361341; Bone et al., *J. Am. Chem. Soc.*, 113, 9382(1991)). Such compounds are, however, reversible inhibitors having limited activities. Irreversible inhibitors which can block the protease activity permanently would be more effective in treating AIDS.

The inventors have made efforts for the development of irreversible inhibitors by way of synthesizing and testing a new class of compounds having a cis-epoxide group which can bind permanently to the reaction site of HIV protease (Korean Patent Application No. 93-10811).

SUMMARY OF THE INVENTION

Accordingly, it is a primary object of the present invention to provide novel compounds having improved inhibitory activity against HIV and a process for the preparation thereof.

Another object of the present invention is to provide compositions comprising the above compounds as active ingredients, useful for the prevention or treatment of AIDS or HIV infection.

In accordance with one aspect of the present invention, there is provided a novel cis-epoxide compound of formula (I) and the pharmacologically acceptable salts, hydrates and solvates thereof:

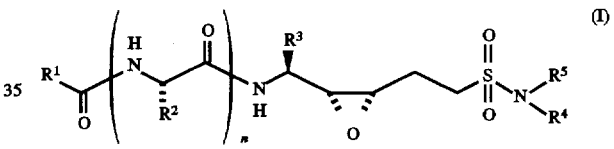

wherein:

$R^1$ is an aromatic group, a nitrogen-containing aromatic group, $C_{1-4}$ alkyl group optionally substituted with an aromatic group or a nitrogen-containing aromatic group, $C_{1-4}$ alkoxy group optionally substituted with an aromatic group or a nitrogen-containing aromatic group;

$R^2$ is an amino acid residue or a $C_{1-8}$ alkyl group substituted with a $C_{1-4}$ alkylsulfonyl group;

$R^3$ is a $C_{1-4}$ alkyl group optionally substituted with an aromatic group;

$R^4$ is hydrogen or a $C_{1-4}$ alkyl group;

$R^5$ is an aromatic group, a $C_{1-10}$ alkyl group or a $C_{1-4}$ alkyl group optionally substituted with an aromatic group; and n is 1 or 2.

DETAILED DESCRIPTION OF THE INVENTION

Referring to the novel cis-epoxy compound of formula (I) of this invention, the term "aromatic group" means a benzene or naphthalene radical carrying optional substituents and the term "nitrogen-containing aromatic group" refers to a pyridine or quinoline radical carrying optional substituents. It must also be understood that the compound of formula (I) may have a plurality of chiral carbons, and accordingly, the compound of the present invention is inclusive of all forms of possible stereoisomers, e.g., an optically pure single isomer, a racemic mixture, a diastereomeric mixture, etc.

In accordance with one embodiment of this invention, $R^1$ is preferably a phenyl, benzyl, quinolyl, quinolylmethyl, phenoxy, benzyloxy, quinolyloxy, quinolylmethoxy, phenoxymethyl or quinolyloxymethyl group; most preferably a quinolyl, benzyloxy or 5-isoquinolyloxymethyl group;

$R^2$ is preferably a $C_{1-4}$ alkyl carrying an amido or sulfone functional group; most preferably an asparagine residue or a 2-methanesulfonyl-2-propyl group;

$R^3$ is preferably a $C_{1-2}$ alkyl substituted with a phenyl group carrying optional substituents; most preferably a benzyl group;

$R^4$ is preferably hydrogen, a methyl, ethyl, n-propyl, iso-propyl, n-butyl, sec-butyl, iso-butyl or t-butyl group; most preferably hydrogen, a methyl or ethyl group; and $R^5$ is preferably a methyl, ethyl, n-propyl, iso-propyl, n-butyl, sec-butyl, iso-butyl, t-butyl, 2,4-dimethyl-3-pentyl, phenyl carrying optional substituents or benzyl carrying optional ring substituents; most preferably a phenyl, iso-propyl, t-butyl or 2,4-dimethyl-3-pentyl group.

Examples of the most desirable compounds according to the present invention are illustrated below:

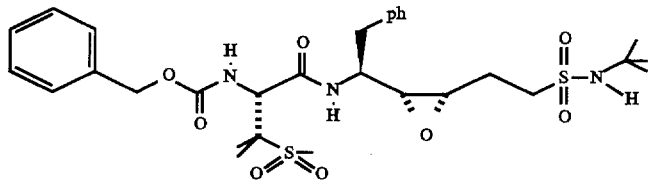

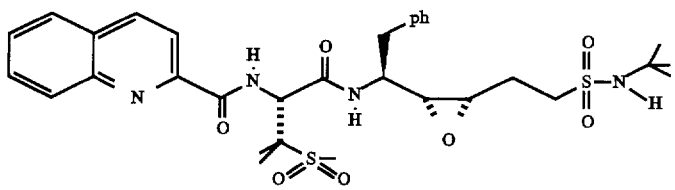

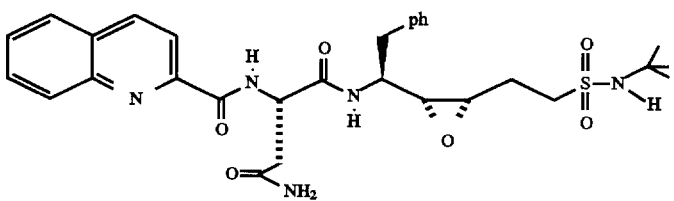

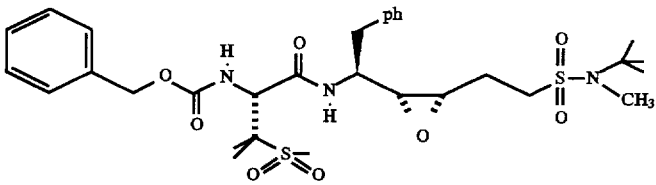

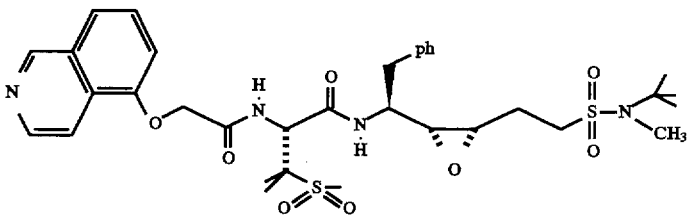

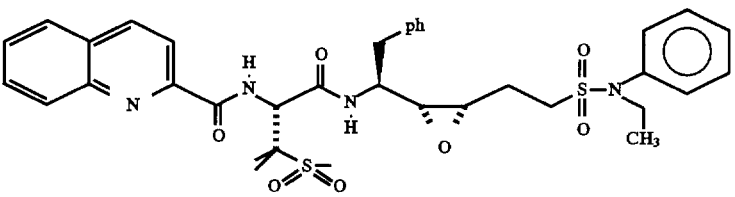

-continued

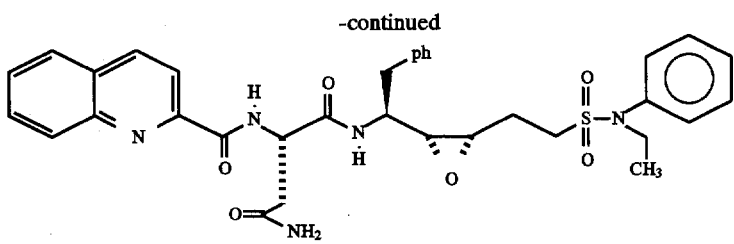

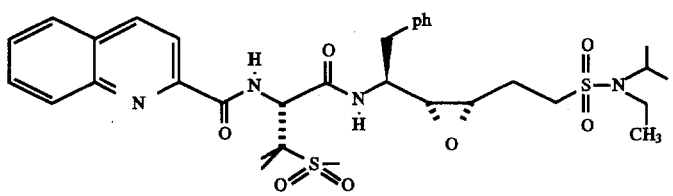

and

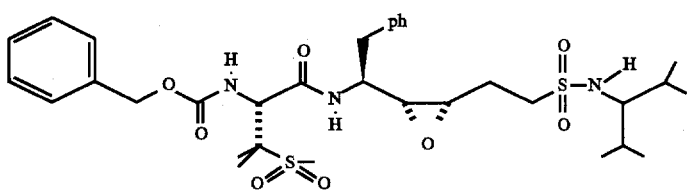

The compound of the formula (I) of the present invention may be prepared as in Scheme 1.

Scheme 1

Step 1:

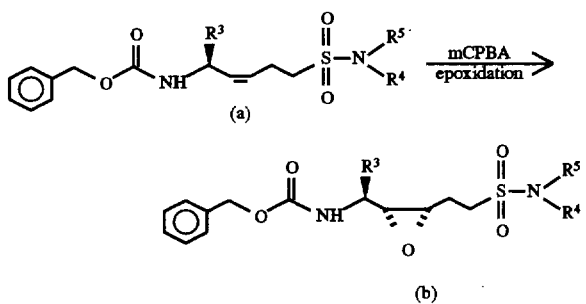

Step 2:

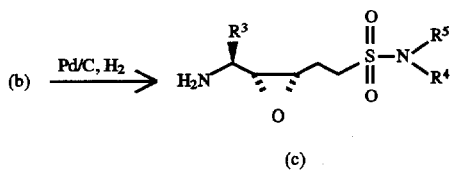

wherein:
$R^6$ is a $C_{1-4}$ alkylgroup;
$R^7$ is a $C_{1-4}$ alkylgroup; and
$R^1$, $R^2$, $R^3$, $R^4$ and $R^5$ have the same meaning as defined previously.

In Step 1 of Scheme 1, the compound of formula (a) is epoxidized with meta-chloroperoxybenzoic acid(mCPBA) to obtain the compound of formula (b). The benzyloxycarbonyl protecting group is removed from the compound of formula (b) to give the compound of formula (c) in Step 2.

Subsequently in Step 3, the compound of formula (c) is coupled with the compound of formula (d) using a coupling agent, followed by oxidation to give the compound of formula (e). The benzyloxycarbonyl protecting group of formula (e) is removed in Step 4 to obtain the compound of formula (f). Then, the compound of formula (f) is coupled with the compound of formula (g) using a coupling agent to give the desired compound of formula (I) in Step 5.

Alternatively, the compound of formula (c) is coupled with the compound of formula (h) to give the desired compound of formula (I) in Step 5'.

In the above coupling reaction, coupling reagents may comprise, but not limited to, dicyclohexylcarbodiimide (DCC), 3-ethyl-3'-(dimethylamino)-propylcarbodiimide (EDC), bis-(2-oxo-3-oxazolidinyl)-phosphinic acid chloride (BOP-Cl), diphenylphosphorylazide (DPPA) and the like.

A carboxylic acid may be converted into an acid halide or an active ester derivative before carrying out a coupling reaction. Such acid halide derivatives include acid chloride, and suitable active ester derivatives are those commonly used to activate a carboxylic acid group for coupling with an amine to form an amide bond, or with an alcohol to form an ester bond: alkoxycarbonyl halides such as methoxycarbonyl chloride, isobutoxycarbonyl chloride, and the like; carboxylic acid anhydrides derived from coupling reagents, and, esters derived from N-hydroxy-benzotriazole, N-hydroxyphthalimide, N-hydroxysuccinimide, N-hydroxy-5-norbornene-2',3'-dicarboxamide and 2,4,5-trichlorophenol; and the like.

The removal of the benzyloxycarbonyl group may be carried out in accordance with a known method in the art, e.g., hydrogenolysis in the presence of a Pd/C catalyst under a $H_2$ pressure.

The compound of formula (a) may be prepared by reacting the compound of formula (j) with N-benzyloxycarbonyl phenylalanal in the presence of potassium hexamethyldisilazane (KHMDS) at $-78°$ C. as illustrated in Scheme 2:

Scheme 2

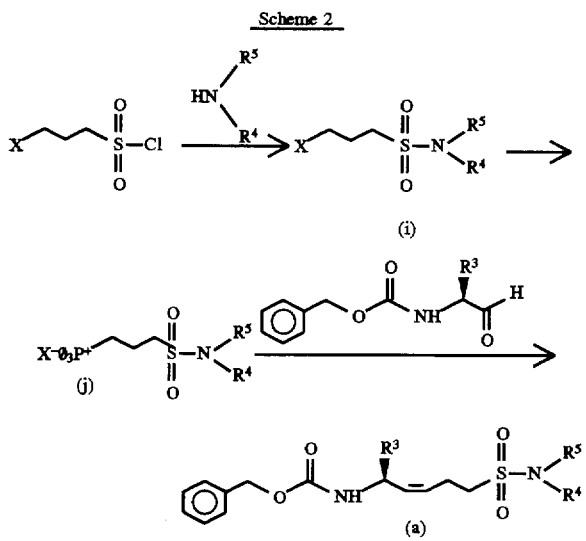

wherein:

X is a halogen atom; and

R³, R⁴ and R⁵ have the same meaning as defined previously.

The compound of formula (i) may be prepared in accordance with a conventional method illustrated in Scheme 3.

Scheme 3

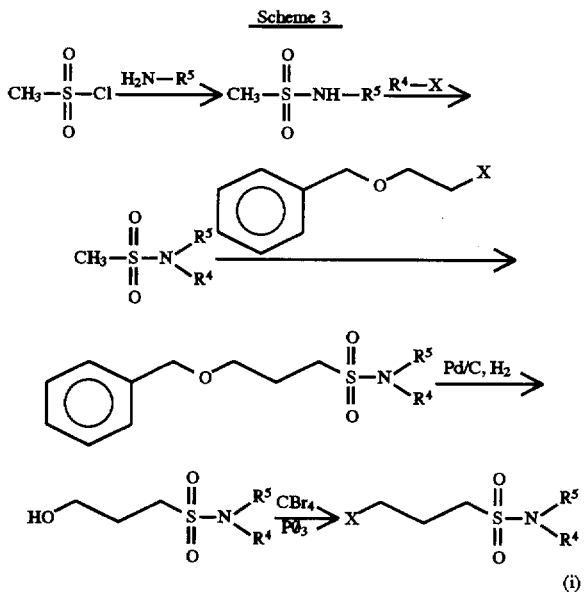

wherein:

R⁴, R⁵ and X have the same meaning as defined previously.

The compound of formula (d) may be prepared as in Scheme 4.

Scheme 4

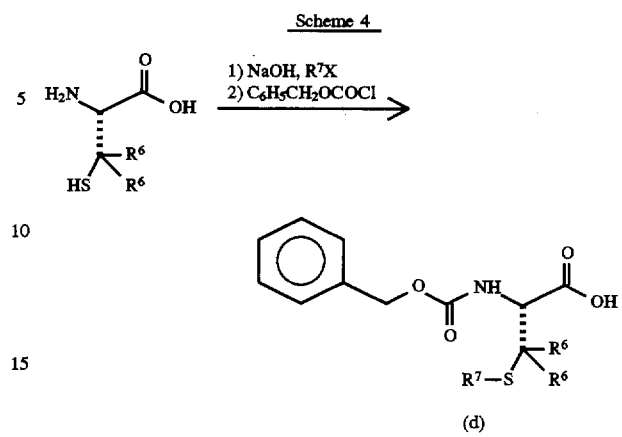

wherein:

R⁶, R⁷ and X have the same meaning as defined previously.

In Scheme 4, the thiol group of substituted cysteine is alkylated under a basic condition and then the amine group is protected with a benzyloxycarbonyl group.

The compound of formula (I) of the present invention may be used for the prevention or treatment of AIDS or HIV infection because it has inhibitory activity against HIV protease. The amount thereof which may be administered to a patient may range from 100 to 600 mg/kg of body weight every 24 hours for a period prescribed to treat the disease. The dosage may be adjusted based on all relevant factors, e.g., the patient's weight, age, sex, healthy condition, diet, excretion rate, mixing with other medicines; the kind and severity of the disease; the type of formulation; the compound used and the administration method thereof and others.

The compositions of the present invention may be administered orally or by injection. Suitable injection solutions, e.g., aqueous or oily suspensions for sterilized injections, may be prepared according to a conventional method by using suitable dispersing agents, hydrating agents or suspending agents. The solvents which may be used in the present invention include polyethyleneglycol, ethyleneglycol, polypropyleneglycol, ethanol and the like.

Solid compositions for oral administration may be in the form of capsules, tablets, pills, powders and granules; the form of capsules is more preferred. In case of tablets, it is advantageous to produce them in the enteric-coated form. These compositions may include one or more inert diluents such as sucrose, lactose and starch, and a lubricant such as magnesium stearate.

The compounds of the present invention may be administered simultaneously with one or more other anti-AIDS agents or immunomodulators.

The compositions comprising the compounds of the present invention for the prevention and the treatment of HIV infection are not limited to those mentioned above, and other pharmaceutical composition containing the compounds of the present invention may be used for the prevention and the treatment of HIV infection.

The following Preparation Examples and Examples are provided for purposes of illustrating certain aspects of the present invention only; they are not to be construed as limiting the scope of the present invention in any way.

PREPARATION EXAMPLE 1

Preparation of N-benzyloxycarbonyl-β-(S-methyl)-L-valine 8.9 g (0.06 mol) of β-mercapto-L-valine was added to a mixture of 120 ml of dioxane and 40 ml of water, cooled to 0° C. and then 20 ml of 6N NaOH aqueous solution was added. 9.24 g (0.066 mol) of methyl iodide was added to the resulting solution and the mixture was stirred for 3 hours at 0° C. and then 2 hours at room temperature to carry out the methylating reaction. The resulting methylated product was cooled to 0° C., and 15 ml of NaOH aqueous solution and 10.2 g (0.09 mol) of benzyl chloroformate were added slowly thereto. After stirring the mixture for 1 hour at 0° C. and 2 hours at 5° C., the reaction was terminated and the solvent was distilled off under a reduced pressure. In order to decompose residual benzyl chloroformate, a mixture of water and ether was added to the distillation residue, stirred and the organic layer was discarded. To the aqueous layer was added 60 ml of ethyl acetate and the mixture was adjusted to below pH 3 with 6N HCl. The organic layer was separated and dried over anhydrous $MgSO_4$, and the solvent was removed by distillation under a reduced pressure to obtain 14.25 g of the title compound(yield 80%).

$^1H$ NMR ($CD_3OD$) δ 1.2(s, 6H), 2.1(s, 3H), 4.3(d, 1H), 5.1(s, 2H), 7.1(m, 5H)

PREPARATION EXAMPLE 2

Preparation of N-ethyl-N-phenyl-5-L-(N-benzyloxycarbonyl)amino-6-phenyl-(4R,3S)-epoxyhexane sulfonamide 2-1) Preparation of N-ethyl-N-phenylmethanesulfonamide 16.7 g(100 mmol) of N-phenylmethanesulfonamide and 27.6 g (212 mmol) of $K_2CO_3$ were dissolved in 200 ml of dimethylform-amide(DMF) and the resulting solution was cooled to 0° C. 11.7 g(110 mmol) of ethylbromide was added dropwise thereto, which was stirred for over 10 hours at room temperature. DMF was distilled off under a reduced pressure and the residue was dissolved in dichloromethane. The resulting solution was washed with water and the organic layer was dried over anhydrous $MgSO_4$. The organic solvent was distilled off under a reduced pressure to obtain 17.9 g of the title compound(yield 92%).

2-2) Preparation of N-ethyl-N-phenyl-3-benzyloxypropane sulfonamide 9.7 g(50mmol) of the compound obtained in Preparation Example 2-1) was dissolved in 50 ml of anhydrous tetrahydrofuran(THF) and the resulting solution was cooled to −78° C. 1.1 equivalents of N-butyllithium was added dropwise thereto and the mixture was stirred for 1 hour. To the resulting solution, 10.6 g(50 mmol) of 1-benzyloxy-2-bromoethane dissolved in 100 ml of anhydrous THF was added dropwise at −78° C. and the whole mixture was stirred for 3 hours. The organic solvent was distilled off and the residue was dissolved in dichloromethane. The resulting solution was washed with a saturated $NaHCO_3$ aqueous solution and the organic layer was dried over anhydrous $MgSO_4$. The organic solvent was distilled off under a reduced pressure and the residue was subjected to column choromatography(ethyl acetate:hexane=1:10) to obtain 7.1 g of the title compound (yield 45%).

$^1H$ NMR($CDCl_3$) δ 0.9(t, 3H), 2.1(m, 2H), 2.6–3.4(m, 6H), 4.8(s, 2H), 7.3(m, 10H)

2-3) Preparation of N-ethyl-N-phenyl-3-hydroxypropane sulfonamide 3.3 g(10 mmol) of the compound obtained in Preparation Example 2-2) was dissolved in 100 ml of methanol and 330 mg of 10% Pd/C was added thereto, which was reacted for 2 hours under 1 atmosphere of hydrogen. The resulting solution was passed through cellite to remove the catalyst and the solvent was distilled off under a reduced pressure to obtain 2.28 g of the title compound(yield 95%).

$^1H$ NMR($CDCl_3$) δ 0.9(t, 3H), 1.8(m, 2H), 2.6–3.3(m, 6H), 7.3(m, 10H)

2-4) Preparation of N-ethyl-N-phenyl-3-bromopropane-sulfonamide 2.28 g(9.46 mmol) of the compound obtained in Preparation Example 2-3) and 3.24 g(10 mmol) of carbontetrabromide were dissolved in 94 ml of anhydrous dichlorophenol and 2.6 g(10 mmol) of triphenylphosphine was added dropwise, followed by stirring for 6 hours. The solvent was distilled off and the residue was subjected to column chromatography(ethyl acetate:hexane=1:10) to obtain 2.57 g of the title compound(yield 90%).

$^1H$ NMR($CDCl_3$) δ 0.9(t, 3H), 1.8(m, 2H), 2.8–3.6(m, 6H), 7.2(m, 10H)

2-5) Preparation of N-ethyl-N-phenyl-3-triphenylphosphonium propanesulfonamide bromide 2.57 g(8.5 mmol) of the compound obtained in Preparation Example 2-4) and 3 equivalents of triphenylphosphine were dissolved in 85 ml of anhydrous acetonitrile and refluxed for 24 hours. The solvent was distilled off and the remaining triphenylphosphine was removed by washing with diethylether to obtain 3.8 g of the title compound(yield 80%).

2-6) Preparation of N-ethyl-N-phenyl-5-L-(N-benzyloxy carbonyl)amino-6-phenyl-hex-3-(cis)-enesulfonamide 3.8 g(6.6 mmol) of the compound obtained in Preparation Example 2-5) was dissolved in 40 ml of THF and the resulting solution was stirred at −78° C. 14.5 ml(0.11 mmol) of 0.5M potassium hexamethylsilazane solution was added thereto and the temperature was maintained at −78° C. for 1 hour. To the resulting solution, 1.86 g(6.6 mmol) of (S)-2-benzyloxycarbonyl amino-3-phenyl-1-propanal dissolved in 30 ml of anhydrous THF was added slowly over 20 minutes. The mixture was stirred for 1 hour at −78° C. and then for additional 1 hour at room temperature. The reaction was quenched by adding water, the solvent was removed and the residue was dissolved in 200 ml of dichloromethane. The resulting solution was washed with a saturated $NaHCO_3$ aqueous solution and the organic layer was dried over $Na_2SO_4$ and subjected to column chromatography (hexane:ethyl acetate=70:30) to obtain 2.53 g of the title compound(yield 78%).

$^1H$ NMR($CDCl_3$) δ 0.9(t, 3H), 2.2(m, 2H), 2.8–3.6(m, 8H), 4.3(m, 1H), 4.8(br, 1H), 5.1(s, 2H), 5.2–5.4(m, 2H), 7.1–7.5(m, 10H).

2-7) Preparation of N-ethyl-N-phenyl-5-L-(N-benzyloxycarbonyl) amino-6-phenyl-(4R,3S)-epoxyhexanesulfonamide 2.53 g (5.14 mmol) of the compound obtained in Preparation Example 2-6) was dissolved in 25 ml of dichloromethane and 2.5 equivalents of meta-chloroperoxybenzoic acid(mCPBA) was added thereto, followed by stirring for 24 hours at room temperature. Approximately 100 ml of 10% $Na_2S_2O_3$ aqueous solution was added and the resulting mixture was stirred for 30 minutes. The organic layer was washed with a saturated $NaHCO_3$ solution and dried over $MgSO_4$. The organic solvent was removed to obtain 1.85 g of the title compound (yield 71%).

$^1H$ NMR($CDCl_3$) δ 0.9(t, 3H), 1.8(m, 2H), 2.6–3.6(m, 10H), 4.0(m, 1H), 4.8(br, 1H), 5.1(s, 2H), 7.1–7.5(m, 10H).

PREPARATION EXAMPLE 3

Preparation of N-t-butyl-5-L-(N-benzyloxycarbonyl)amino-6-phenyl-(4R,3S)-epoxyhexane sulfonamide 3-1) Preparation of N-t-butyl-5-L-(N-benzyloxycarbonyl)amino-6-phenyl-hex-3-(cis)-enesulfonamide 67.6 g(0.12 mol) of N-t-butyl-3-triphenylphosphonium propane sulfonamide chloride was dissolved in 400 ml of THF and the resulting solution was stirred at −78° C. 440 ml(0.22 mol) of 0.5M potassium hexamethylsilazane solution was added thereto and the whole mixture was maintained at −78° C. for 1 hour. To the resulting solution, 28.3 g(0.1 mol) of (S)-2-benzyloxycarbonylamino-3-phenyl-1-propanal was added slowly and the mixture was stirred for 1 hour at −78° C. and then for additional 1 hour at room temperature. The reaction was quenched by adding water, the solvent was removed and the residue was dissolved in 240 ml of dichloromethane. The resulting solution was washed with a saturated $NaHCO_3$ solution and then with water and the organic layer was dried over anhydrous $Na_2SO_4$ and subjected to column chromatography (hexane:ethyl acetate=70:30) to obtain 24.9 g of the title compound(yield 51%).

$^1$H NMR($CDCl_3$) δ 1.4(s, 9H), 2.4–3.0(m, 6H), 4.1(br, 1H), 4.4(m, 1H), 5.1(m, 3H), 5.2(t, 1H), 5.3(m, 1H), 7.0–7.4 (m, 10H).

3-2) Preparation of N-t-butyl-5-L-(N-benzyloxycarbonyl)amino-6-phenyl-(4R,3S)-epoxyhexanesulfonamide 4.4 g (10 mmol) of the compound obtained in Preparation Example 3-1) was dissolved in 25 ml of dichloromethane and 2.5 equivalents of meta-chloroperoxybenzoic acid was added thereto, followed by stirring for 24 hours at room temperature. Approximately 100 ml of 10% $Na_2S_2O_3$ aqueous solution was added and the resulting mixture was stirred for 30 minutes. The organic layer was washed with a saturated $NaHCO_3$ solution. The organic layer was dried over anhydrous $MgSO_4$ and the solvent was removed to obtain 3.81 g of the title compound(yield 83%).

$^1$H NMR($CDCl_3$) δ 1.4(s, 9H), 1.8(m, 2H), 2.8–3.2(m, 6H), 3.8(m, 1H), 4.2(br, 1H), 5.0(m, 3H), 7.1–7.4(m, 10H).

PREPARATION EXAMPLE 4

Preparation of N-t-butyl-N-methyl-5-L-(N-benzyloxycarbonyl)amino-6-phenyl-(4R,3S)-epoxyhexane sulfonamide 4-1) Preparation of N-t-butyl-N-methyl-3-chloropropane sulfonamide 1.74 g(0.02 mol) of t-butylmethylamine and 2 equivalents of triethylamine were dissolved in 100 ml of dichloromethane, which was stirred at 0° C. 3.54 g(0.02 mol) of 3-chloropropane sulfonyl chloride dissolved in 50 ml. of dichloromethane was added dropwise and the mixture was stirred for 1 hour at room temperature. The organic layer was washed with 1N HCl aqueous solution and dried over $MgSO_4$ to obtain 3.31 g of the title compound(yield 73%).

$^1$H NMR($CDCl_3$) δ 1.4(s, 9H), 2.2(m, 2H), 2.8(s, 3H), 3.3(m, 2H), 3.8(m, 2H)

4-2) Preparation of N-t-butyl-N-methyl-3-triphenylphosphonium propanesulfonamide chloride A mixture of 2.27 g(10 mmol) of the compound obtained in Preparation Example 4-1) and 11.3 g(50 mmol) of triphenyl phosphine was left standing for 10 hours at 130° C. The excess triphenylphosphine was removed by washing with diethylether. After drying under a reduced pressure, 4.16 g of the title compound was obtained(yield 92%).

$^1$H NMR($CDCl_3$) δ 1.4(s, 9H), 2.2(m, 2H), 2.8(s, 3H), 3.6(m, 2H), 4.1(m, 1H), 4.3(m, 1H), 7.1(m, 5H), 7.4(m, 15H)

4-3) Preparation of N-t-butyl-N-methy-5-L-(N-benzyloxy carbonyl)amino-6-phenyl-hex-3-(cis)-enesulfonamide 6.52 g(12 mmol) of the compound obtained in Preparation Example 4-2) was dissolved in 40 ml of THF and the resulting solution was stirred at −78° C. 22 ml (11 mmol) of 0.5M potassium hexamethylsilazane was added thereto and the mixture was maintained at −78° C. for 1 hour. To the resulting solution, 2.83 g(10 mmol) of (S)-2-benzyloxycarbonylamino-3-phenyl-1-propanal dissolved in 10 ml of anhydrous THF was added slowly over 20 minutes and the mixture was stirred for 1 hour at −78° C. and then for additional 1 hour at room temperature. The reaction was quenched by adding water, the solvent was removed and the residue was dissolved in 100 ml of dichloromethane. The resulting solution was washed with a saturated $NaHCO_3$ solution and then with water and the organic layer was dried over anhydrous $Na_2SO_4$ and subjected to column chromatography (hexane:ethyl acetate=70:30) to obtain 3.83 g of the title compound(yield 84%).

$^1$H NMR($CDCl_3$) δ 1.4(s, 9H), 2.4–3.0(m, 9H), 4.4(m, 1H), 4.5(br, 1H), 5.1(s, 2H), 5.2(t, 1H), 5.3(m, 1H), 7.0–7.4 (m, 10H).

4-4) Preparation of N-t-butyl-N-methyl-5-L-(N-benzyloxy carbonyl)amino-6-phenyl-(4R,3S)-epoxyhexanesulfonamide 4.57 g (10 mmol) of the compound obtained in Preparation Example 4-3) was dissolved in 25 ml of dichloromethane and 2.5 equivalents of meta-chloroperoxybenzoic acid was added thereto, followed by stirring for 24 hours at room temperature. Approximately 20 ml of 10% $Na_2S_2O_3$ aqueous solution was added and the resulting mixture was stirred for 30 minutes. The organic layer was washed with a saturated $NaHCO_3$ solution, dried over anhydrous $MgSO_4$ and the solvent was removed to obtain 4.11 g of the title compound(yield 87%).

$^1$H NMR($CDCl_3$) δ 1.4(s, 9H), 1.8(m, 2H), 2.8–3.2(m, 9H), 3.8(m, 1H), 5.0(m, 3H), 7.1–7.4(m, 10H).

EXAMPLE 1

Preparation of N-t-butyl-5S-[N-benzyloxy-carbonyl-β-methanesulfonyl-L-valinyl]amino-(4R,3S)-epoxy-6-phenylhexanesulfonamide 283 mg (0.6 mmol) of the compound obtained in Preparation Example 3-2) was dissolved in 20 ml of methanol and approximately 28 mg of 10% Pd/C was added thereto and the mixture was stirred for 6 hours under 1 atmosphere of hydrogen (rubber balloon). After removing the catalyst from the solution by passing through cellite, the solvent was distilled off under a reduced pressure. 198 mg (0.5 mmol) of N-benzyloxy-carbonyl-β-(S-methyl)-L-valin and 1.5 equivalents each of 3-ethyl-3'-(diethylamino)-propylcarbodiimide(EDC) and N-hydroxy-benzotriazole (HOBT) were dissolved in 10 ml of dimethylformamide (DMF) and the amine obtained above was added thereto at 0° C. The resulting mixture was stirred for 6 hours at room temperature and the solvent was distilled off under a reduced pressure. The residue was dissolved in 100 ml of dichloromethane and the resulting solution was washed with a saturated $NaHCO_3$ solution. The organic layer was dried over anhydrous $MgSO_4$ and the solvent was removed. 10 ml of dichloromethane and 5 equivalents of meta-chloroperoxybenzoic acid were added to the residue and the mixture was stirred for 30 minutes. The organic layer was washed with a saturated $NaHCO_3$ solution and dried over anhydrous $MgSO_4$. After removing the solvent by distillation under a reduced pressure, column chromatography (hexane:ethyl acetate=70:30) was carried out to obtain 239 mg of the title compound(yield 75%).

$^1$H NMR($CDCl_3$) δ 1.41(s, 9H), 1.52(s, 3H), 1.63(s, 3H), 1.84(m, 2H), 2.95(m, 9H), 3.96(m, 1H), 4.17(br, 1H), 4.68 (d, 1H), 5.09(s, 2H), 6.01(br, 1H), 7.02(br, 1H), 7.13–7.44 (m, 10H)

MS (FAB, m/e) 638(M+1)

EXAMPLE 2

Preparation of N-t-butyl-5S-[N-(2-quinoline carbonyl)-β-methanesulfonyl-L-valinyl]amino-(4R,3S)-epoxy-6-phenylhexanesulfonamide 254 mg (0.4 mmol) of the compound obtained in Example 1 was dissolved in 20 ml of methanol and approximately 25 mg of 10% Pd/C was added thereto and the mixture was stirred for 6 hours under 1 atmosphere of hydrogen(rubber balloon). After removing the catalyst from the solution by passing through cellite, the solvent was distilled off under a reduced pressure. 696 mg (0.4 mmol) of 2-quinolinecarboxylic acid and 1.5 equivalents each of EDC and HOBT were dissolved in 10 ml of DMF and the amine obtained above was added thereto at 0° C. The resulting mixture was stirred for 6 hours at room temperature and the solvent was distilled off under a reduced pressure. The residue was dissolved in 100 ml of methylenechloride and the resulting solution was washed with a saturated $NaHCO_3$ solution and dried over anhydrous $MgSO_4$. After removing the solvent, column chromatography(ethyl acetate) was carried out to obtain 183 mg of the title compound(yield 70%).

$^1H$ NMR($CDCl_3$) δ 1.41(s, 9H), 1.62(m, 8H), 2.93–3.04 (m, 9H), 4.05(s, 3H), 4.16(br, 1H), 5.07(d, 1H), 7.08–7.49 (m, 6H), 7.81–8.02(m, 3H), 8.13–8.34(m, 3H), 9.25(br, 1H)

MS (FAB, m/e) 657(M+1)

EXAMPLE 3

Preparation of N-b-butyl]-5S-[N-(2-quinolinecarbonyl)-L-asparaginyl]amino-(4R,3S)-epoxy-6-phenylhexanesulfonamide A similar procedure as in Example 1 was used to preprared the title compound.

$^1H$ NMR($CDCl_3$) δ 1.3(m,9H), 1.81(m,2H), 2.93–3.1(m, 6H), 4.1(m, 1H), 4.92(s, 1H), 5.1(m, 1H), 5.8(br, 1H), 6.2(br, 1H), 7.1–8.4(m, 12H), 9.41(d, 1H)

MS (FAB, m/g) 596(M+1)

EXAMPLE 4

Preparation of N-t-butyl-N-methyl-5S-[N-benzyloxycarbonyl-β-methanesulfonyl-L-valinyl]amino-(4R,3S)-epoxy-6-phenyl-hexanesulfonamide 473 mg (1 mmol) of the compound obtained in Preparation Example 4-4) was dissolved in 20 ml of methanol and approximately 47 mg of 10% Pd/C was added thereto and the mixture was stirred for 3 hours under 1 atm of hydrogen (rubber balloon). After removing the catalyst from the solution by passing through cellite, the solvent was distilled off under a reduced pressure. 279 mg (1 mmol) of N-banzyloxycarbonyl-β-(S-methyl)-L-valin and 1.5 equivalents each of EDC and HOBT were dissolved in 10 ml of DMF and the amine obtained above was added thereto at 0° C. The resulting mixture was stirred for 6 hours at room temperature and the solvent was distilled off under a reduced pressure. The residue was dissolved in dichloromethane and the resulting solution was washed with a saturated $NaHCO_3$ solution. The organic layer was dried over anhydrous $MgSO_4$. 5 equivalents of meta-chloroperoxy- benzoic acid was added thereto and the mixture was stirred for 2 hours at room temperature and the organic layer was washed with a 10% $NaHCO_3$ solution and dried over anhydrous $MgSO_4$. After removing the solvent by distillation under a reduced pressure, column chromatography(hexane:ethyl acetate= 70:30) was carried out to obtain 488 mg of the title compound(yield 75%).

$^1H$ NMR($CDCl_3$) δ 1.4–1.8(m, 17H), 2.8–3.0(m, 12H), 3.9(m, 1H), 4.56(br, 1H), 5.1(s, 1H), 6.04(br, 1H), 7.0(br, 1H), 7.1–7.4(m, 10H)

MS (FAB, m/e) 652(M+1)

EXAMPLE 5

Preparation of N-t-butyl-N-methyl-5 S-[N-(5-isoquinolyloxymethylcarbonyl)-β-methanesulfonyl-L-valinyl]amino- (4R,3S)-epoxy-6-phenylhexanesulfonamide 260 mg (0.4 mmol) of the compound obtained in Example 1 was dissolved in 20 ml of methanol and approximately 26 mg of 10% Pd/C was added thereto and the mixture was stirred for 6 hours under 1 atm of hydrogen(rubber balloon). After removing the catalyst from the solution by passing through cellite, the solvent was distilled off under a reduced pressure. 81.2 mg (0.4 mmol) of 5-isoquinolyloxyacetic acid and 1.5 equivalents each of EDC and HOBT were dissolved in 100 ml of DMF and the amine obtained above was added thereto at 0° C. The resulting mixture was stirred for 6 hours at room temperature and the solvent was distilled off under a reduced pressure. The residue was dissolved in 100 ml of methylenechloride and the solution was washed with a saturated $NaHCO_3$ solution. The organic layer was dried over anhydrous $MgSO_4$. After removing the solvent, column chromatography(ethyl acetate) was carried out to obtain 196 mg of the title compound(yield 70%).

$^1H$ NMR($CDCl_3$) δ 1.4(s, 9H), 1.56(s, 3H), 1.6(s, 3H), 1.8(m, 2H), 3.0(m, 12H), 4.0(m, 1H), 4.83(s, 2H), 5.0(d, 1H), 7.0(br, 1H), 7.1–7.3(m, 6H), 7.4(m, 2H), 8.0(t, 2H), 8.4(d, 1H), 9.2(br, 1H)

MS (FAB, m/e) 703(M+1)

EXAMPLE 6

Preparation of N-ethyl-N-phenyl-5S-[N-(2-quinolinecarbonyl)-β-methanesulfonyl-L-valinyl]amino- (4R, 3S)-epoxy-6-phenylhexanessulfonamide The title compound was prepared from the compound obtained in Preparation Example 2-7) in accordance with procedure described in Example 1.

$^1H$ NMR($CDCl_3$) δ 1.1(t, 3H), 1.4–1.8(m, 8H), 2.8–3.13 (m, 9H), 3.6(m, 2H), 3.92(m, 1H), 5.1(d, 1H), 7.1–8.3(m, 12H), 9.4(d, 1H)

MS (FAB, m/e) 707(M+1)

EXAMPLE 7

Preparation of N-ethyl-N-phenyl-5S-[N-(2-quinolinecarbonyl)-L-asparaginyl]amino-(4R, 3S)-epoxy-6-phenylhexanesulfonaimide The title compound was prepared from the compound obtained in Preparation Example 2-7) in accordance with procedure described in Example 1.

$^1H$ NMR($CDCl_3$) δ 1.1(t, 3H), 1.2(m, 12H), 2.6–3.3(m, 8H), 3.67(m, 2H), 4.03(m, 1H), 5.1(m, 1H), 5.3(br, 1H), 7.02–7.4(m, 6H), 7.5–8.3(m, 6H), 9.2(d, 1H)

MS (FAB, m/e) 646(M+1)

EXAMPLE 8

Preparation of N-ethyl-N-isopropyl-5S-[N-(2-quinolinecarbonyl)-β-methanesulfonyl-L-valinyl]amino- (4R, 3S)-epoxy-6-phenylhexane-sulfonamide A similar procedure as in Example 1 was used to preprared the title compound.

$^1H$ NMR($CDCl_3$) δ 1.3(m, 9H), 1.82(m, 8H), 2.8–3.23(m, 11H), 4.0(m, 2H), 5.1(d, 2H), 7.12–7.34(m, 6H), 7.4–8.3(m, 6H), 9.34(d, 1H)

MS (FAB, m/e) 673(M+1)

EXAMPLE 9

Preparation of N-(2,4-dimethyl-3-pentyl)-5S-[N-(2-benzyloxycarbonyl)-β-methanesulfonyl-L-valinyl] amino-(4R,3S)-epoxy-6-phenylhexane-sulfonamide A similar procedure as in Example 1 was used to prepared the title compound.

$^1$H NMR(CDCl$_3$) δ 0.9(m, 12H), 1.42–1.87(m, 10H), 2.93–3.1(m, 10H), 4.1(m, 1H), 4.6(d, 1H), 5.12(s, 2H), 6.0(d, 1H), 7.0(d, 1H), 7.12–7.43(m, 11H)
MS (FAB, m/e) 680(M+1)

Assay for Inhibitory Effect on HIV Protease

The inhibitory effect on HIV protease of the compounds of the present invention was determined by the following method.

To a buffer solution comprising 50 mM sodium acetate, pH 5.5, 1 mM dithiothreitol(DTT), 1 mM ethylenediaminetetra-acetate (EDTA), 0.75M ammonium sulfate, 0.2M sodium chloride and 0.1% NP40(NONIGET P-40; Sigma Chemical Co., U.S.A.), were added various concentrations of a compound selected from the compound obtained in Examples 1 to 9 to prepare a preincubation solution. Inhibition reaction was started with the addition of 2.6nM of HIV-1 protease to the preincubation solution. Each 10 µl of the reaction solution was taken at a given time interval and added to 80 µl of assay solution containing 100 µM of reaction substrate in the same buffer solution as the above to assay for the residual enzyme activity. In this context, an oligopeptide($K_M$=20 µM) consisting of 11 amino acids, i.e., Ser-Ile-Ala-Glu-(p-NO$_2$)-Phe-Leu-Val-Arg-Ala-Lys-His, was used as a reaction substrate, which oligopeptide was to be cleaved in two by the breakage of amide bond between (P-NO$_2$)-Phe and Leu upon the attack of HIV protease. The reaction rate was determined by subjecting the substrate before the reaction and the product after the reaction to HPLC separation and then measuring the relative amount of the product, using the strong absorbance of (p-NO$_2$)-Phe at 280 nm. The amounts of reduction in enzyme activity according to the elasped time were measured and the natural logarithmic values(ln) of the measured amounts were plotted against time to obtain a linear graph and $k_{obs}$ was calculated from the slope of the linear graph.

The inhibition constant was calculated according to the following equation:

$$\frac{1}{k_{obs}} = \frac{1}{k_{ina}} + \frac{K_I}{k_{ina}} \cdot \frac{1}{[I]}$$

wherein:

$k_{obs}$ is a rate constant indicating the rate of reduction in enzyme activity according to the elapsed time under the presence of a given concentration of inhibitor, $k_{ina}$ is a rate constant indicating the rate of chemical reaction forming covalent bond between an enzyme and an inhibitor in Michaelis-Menten complex, $K_I$ is an inhibition constant indicating the dissociation rate of Michaelis-Menten complex into an enzyme and an inhibitor, and

[I] means the inhibitor concentration.

The above equation is applicable to an experiment carried out under the condition in which the concentration of inhibitor is far higher than that of enzyme (Steady State Kinetic). In case that the experiment was carried out under the condition in which the concentrations of inhibitor and enzyme were about the same, because of the superior inhibition effect of the inhibitor, the mechanism equation of

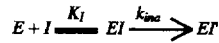

$$E + I \xrightarrow{K_I} EI \xrightarrow{k_{ina}} EI'$$

(wherein, E means an enzyme, I means an inhibitor, EI means a Michaelis-Menten complex and EI' means a complex having convalent bond formed between an enzyme and an inhibitor; and $K_I$ and $k_{ina}$ have the same meanings as defined above) was used to calculate the relative concentration of active enzyme, i.e., [E]/([E]+[EI]+[EI']) in every given time. The inhibition constants $K_I$ and $k_{ina}$ and second order rate constant $k_{ina}/K_I$ were obtained by inputting the value of [E]/([E]+[EI]+[EI']) into KINSIM/FITSIM program. The inhibition constants thus obtained are listed in Table I.

The results in Table I show that each of the compounds of the present invention has a large second order rate constant $k_{ina}/K_I$, which fully demonstrates that an essentially irreversible reaction takes place between HIV protease and the compound of this invention.

Determination of Anti-Viral Activity and Cytotoxicity

The anti-viral activity of the compounds of the present invention was determined by measuring the concentration of the compounds that inhibits the proliferation of HIV by 50%(IC$_{50}$) through a survey for syncytium formation or reverse transcriptase assay.

1×10$^5$ cells of each of H9(ATCC HTB 176) and Sup T1 cell lines were added to the wells of a 24-well microtiter plate and various concentrations of the compounds of the present invention were added thereto. 200 TCID$_{50}$(200-fold of 50% tissue culture infection dose) of HIV-1 inoculum and rpmi-1640 medium(Sigma Chemical Co., U.S.A) were added successively to the wells and the plate was incubated at 37° C. In case of Sup T1, the number of syncytium formed was investigated after 3 to 9 days. IC$_{50}$ of each compound was determined by measuring the concentration of inhibitor that can reduce the number of syncytium by 50% compared with those formed in the same condition without the inhibitor.

In case of H9, three-quarters(¾) of the culture medium in volume was refreshed every 3 days; and after 9 days, 6 ml of the culture fluid was taken and 2.5 ml of 30% polyethyleneglycol(PEG, M.W. 6000–8000) and 0.4M NaCl were added thereto. The resulting solution was allowed to stand at 0° C. overnight to precipitate virus particles. The solution was centrifuged at 2000 rpm for 45 minutes, the supernatant was discarded therefrom and the precipitate was diluted with 20 µl of a reverse transcriptase suspension buffer(50 mM tris-HCl, pH 7.5, 1 mM dithiothreitol, 20% glycerol, 0.25M KCl and 0.25% Triton X-100). The resulting suspension was stored in an Effendorf tube at −70° C. until used. A procedure of freezing said virus suspension for 2 minutes in dry ice and thawing same at 37° C. for 2 minutes was repeated three times and the resulting suspension was centrifuged at 4° C. The resulting supernatant was used in carrying out the reverse transcriptase assay.

10 µl of the said viral suspension was added to a solution of: 10 µl of buffer solution(250 mM tris-HCl, pH 7.5, 37.5 mM MgCl$_2$, 0.25% triton X-100), 1.2 µl of 200 mM dithiothreitol, 5 µl of 100 µM oligo(dT)-poly(A)(Boeringer Manheim, 12–18 oligomer), 1 µl (1 µCi) of $^3$H-TTP (Thymidinetri-phosphate) and 23.6 µl of water; and the resulting mixture was placed at 37° C. After 1 hour, the mixture was poured onto a WHATMAN DEB1 filter and the filter was washed three times with 5 ml of 2×SSC buffer solution(17.53 g of sodium chloride, 8.82 g of sodium citrate, pH 7.0, 1 liter of water) for about 10 minutes each time and twice with 95% methanol for 10 seconds. The filter was put onto aluminium foil and dried with an infra-red lamp. The amount of radioactivity was counted using a liquid scintillation counter.

To determine the cytotoxicity of the compounds of the present invention, 0.1 μM to 100 μM of the novel compounds were added to H9 cell or SupT1 cell and the mixture was cultured on a rpmi-1640 medium at 37° C. The medium was refreshed every 3 days and the extent of cell proliferation was observed using Hemacytometer according to the trypan blue dye exclusion technique which is well known in the art. $CT_{50}$(i.e., concentration that causes death of cells by 50%) was determined. As control compounds, azidothymidine(AZT, Burrows-Wellcome Co.) and Ro-31 8959(Hoffmann-La Roche AG) were used. Table I shows the anti-viral activities($IC_{50}$) and cytotoxicities ($CT_{50}$) of the tested compounds of the present invention.

TABLE I

| | *$k_{inact}/K_I$ (min$^{-1}$M$^{-1}$) | IC (nM) | $CT_{50}$ (μM) |
|---|---|---|---|
| Ex. 1 | $10^9$–$10^{10}$ | 25 | >10 |
| Ex. 2 | $10^9$–$10^{10}$ | 30 | >10 |
| Ex. 3 | $10^9$–$10^{10}$ | 10 | >10 |
| Ex. 4 | $10^9$–$10^{10}$ | 1 | >10 |
| Ex. 5 | $10^9$–$10^{10}$ | 5 | >10 |
| Ex. 6 | $10^9$–$10^{10}$ | 5 | >10 |
| Ex. 7 | $10^9$–$10^{10}$ | 20 | >10 |
| Ex. 8 | $10^9$–$10^{10}$ | 10 | >10 |
| Ex. 9 | $10^9$–$10^{10}$ | 10 | >10 |
| AZT | | 12 | >10 |
| Ro-31-8959 | | 7 | >10 |

*In case that second order rate constant $k_{inact}/K_I$ is larger than $10^9$, it is hard to calculate the exact values by KINSIM/FITSIM program. [Williams, J. W. and Morrison, J. F., Methods, Enzymol., 63, 437–466(1079); and Zimmerle, C. T. and Frieden, C., J. Biochem., 258, 381–387(1989)]

As can be seen from the above results, the compound of formula (I) of the present invention are irreversible HIV protease inhibitors having a high inhibitory effect and low cytotoxicity, and therefore, useful in the prevention or treatment of AIDS or HIV infection.

While the invention has been described with respect to the specific embodiments, it should be recognized that various modifications and changes may be made by those skilled in the art to the invention which also fall within the scope of the invention as defined by the appended claims.

What is claimed is:

1. A cis-epoxide compound of formula (I) and pharmaceutically acceptable salts, hydrates and solvates thereof:

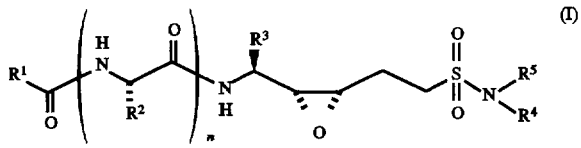

wherein:

R$^1$ is an aromatic group, a nitrogen-containing aromatic group, C$_{1-4}$ alkyl group optionally substituted with an aromatic group or a nitrogen-containing aromatic group, C$_{1-4}$ alkoxy group optionally substituted with an aromatic group or a nitrogen-containing aromatic group;

R$^2$ is an amino acid residue or a C$_{1-8}$ alkyl group substituted with a C$_{1-4}$ alkylsulfonyl group;

R$^3$ is a C$_{1-4}$ alkyl group optionally substituted with an aromatic group;

R$^4$ is hydrogen or a C$_{1-4}$ alkyl group;

R$^5$ is an aromatic group, a C$_{1-10}$ alkyl group or a C$_{1-4}$ alkyl groups optionally substituted with an aromatic group; and n is 1 or 2.

2. The cis-epoxide compound of claim 1, wherein R$^3$ is a benzyl group and n is 1.

3. The cis-epoxide compound of claim 2, wherein R$^1$ is a quinolyl, benzyloxy or 5-isoquinolyloxymethyl group.

4. The cis-epoxide compound of claim 2, wherein R$^2$ is an asparagine residue or a 2-methanesulfonyl-2-propyl group.

5. The cis-epoxide compound of claim 2, wherein R$^5$ is phenyl, iso-propyl, t-butyl or 2,4-dimethyl-3-pentyl group.

6. The cis-epoxide compound of claim 1, which is selected from the group consisting of:

N-t-butyl-5S-[N-benzyloxycarbonyl-β-methanesulfonyl-L-valinyl]amino-(4R, 3S)-epoxy-6-phenylhexanesulfonamide;

N-t-butyl-5S-[N-(2-quinolinecarbonyl)-β-methanesulfonyl-L-valinyl]amino-(4R,3S)-epoxy-6-phenylhexanesulfonamide;

N-t-butyl]-5S-[N-(2-quinolinecarbonyl)-L-asparaginyl]amino-(4R, 3S)-epoxy-6-phenylhexanesulfonamide;

N-t-butyl-N-methyl-5S-[N-benzyloxycarbonyl-β-methanesulfonyl-L-valinyl]amino-(4R, 3S)-epoxy-6-phenylhexanesulfonamide;

N-t-butyl-N-methyl-5S-[N-(5-isoquinolyloxymethylcarbonyl)-β-methanesulfonyl-L-valinyl]amino-(4R, 3S)-epoxy-6-phenylhexanesulfonamide;

N-ethyl-N-phenyl-5S-[N-(2-quinolinecarbonyl)-β-methane-sulfonyl-L-valinyl]amino-(4R, 3S)-epoxy-6-phenylhexanesulfonamide;

N-ethyl-N-phenyl-5S-[N-(2-quinolinecarbonyl)-L-asparaginyl]amino-(4R, 3S)-epoxy-6-phenylhexanesulfonaimide;

N-ethyl-N-isopropyl-5S-[N-(2-quinolinecarbonyl)-β-methane sulfonyl-L-valinyl]amino-(4R,3S)-epoxy-6-phenylhexane sulfonamide; and N-(2,4-dimethyl-3-pentyl)-5S-[N-(2-benzyloxycarbonyl)-β-methanesulfonyl-L-valinyl]amino-(4R,3S)-epoxy-6-phenyl hexanesulfonamide.

7. A process for preparing the compound of formula (I) of claim 1 comprising the steps of: i) epoxidizing a compound of formula (a) with meta-chloroperoxybenzoic acid (mCPBA) to obtain the compound of formula (b); ii) removing the benzyloxycarbonyl protecting group from the compound of formula (b) to give the compound of formula (c); and iii) coupling the compound of formula (c) with the compound of formula (h) to give the desired compound of formula (I):

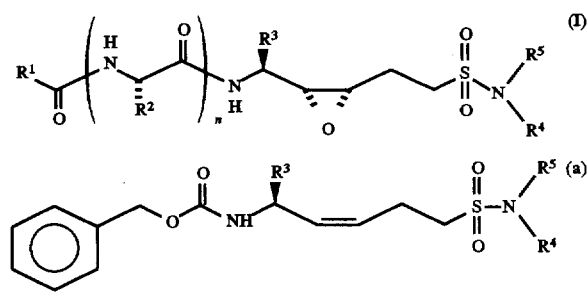

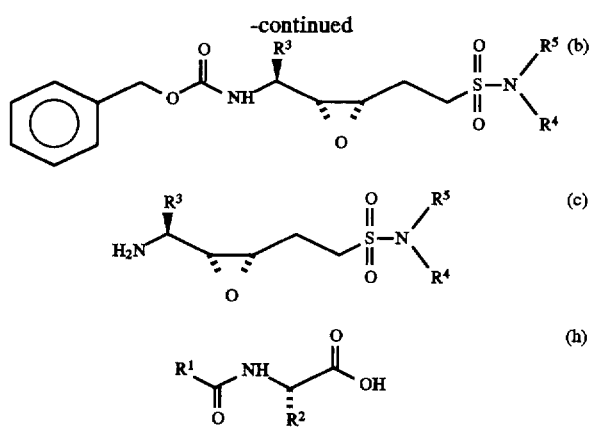

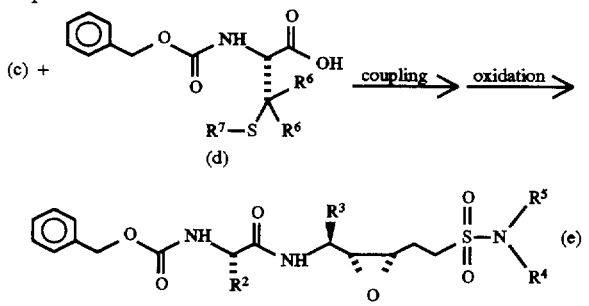

wherein:
R² is an amino acid residue;
R⁶ is a $C_{1-4}$ alkylgroup;
R⁷ is a $C_{1-4}$ alkylgroup; and
R¹, R³, R⁴ and R⁵ have the same meaning as defined in claim 1.

Step 3:

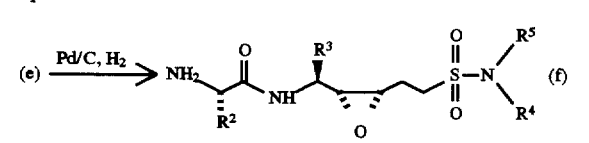

Step 4:

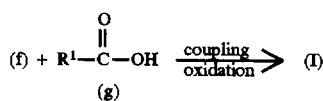

Step 5:

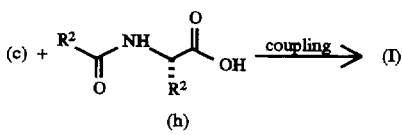

Step 5':

(c) + R²—NH—C(O)—...—OH $\xrightarrow{coupling}$ (I)
(h)

8. A process for preparing the compound of formula (I) of claim 1 comprising the steps of: i) epoxidizing a compound of formula (a) with meta-chloroperoxybenzoic acid (mCPBA) to obtain the compound of formula (b); ii) removing the benzyloxycarbonyl protecting group from the compound of formula (b) to give the compound of formula (c); iii) coupling the compound of formula (c) with the compound of formula (d) using a coupling agent, followed by oxidation to give the compound of formula (e); iv) removing the benzyloxycarbonyl protecting group of formula (e) to obtain the compound of formula (f); and v) coupling the compound of formula (f) with the compound of formula (g) using a coupling agent to give the desired compound of formula (I):

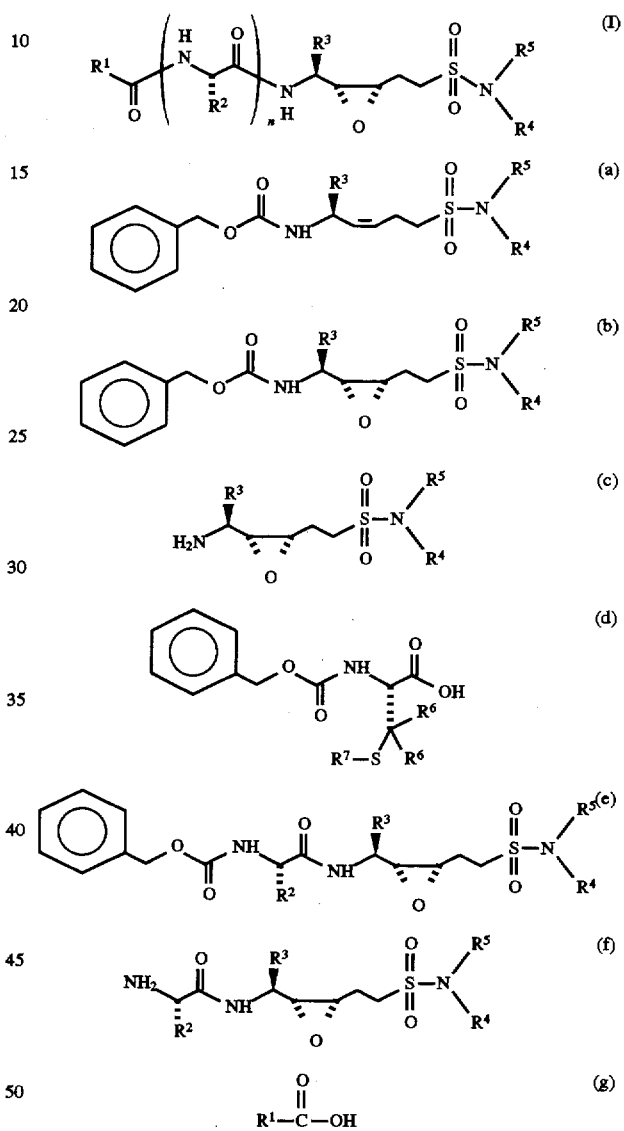

wherein:
R² is a $C_{1-8}$ alkyl group substituted with a $C_{1-4}$ alkylsulfonyl group;
R⁶ is a $C_{1-4}$ alkylgroup;
R⁷ is a $C_{1-4}$ alkylgroup; and
R¹, R³, R⁴ and R⁵ have the same meaning as defined in claim 1.

9. A pharmaceutical composition comprising a therapeutically effective amount of the cis-epoxide compound of claims 1 to 6, pharmaceutically acceptable salts, hydrates or solvates thereof, and a pharmaceutically acceptable carrier.

* * * * *